(12) United States Patent
Hiura et al.

(10) Patent No.: US 8,698,077 B2
(45) Date of Patent: Apr. 15, 2014

(54) METHOD FOR DETERMINING NUMBER OF LAYERS OF TWO-DIMENSIONAL THIN FILM ATOMIC STRUCTURE AND DEVICE FOR DETERMINING NUMBER OF LAYERS OF TWO-DIMENSIONAL THIN FILM ATOMIC STRUCTURE

(75) Inventors: Hidefumi Hiura, Tokyo (JP); Kazuhito Tsukagoshi, Ibaraki (JP); Hisao Miyazaki, Ibaraki (JP)

(73) Assignees: NEC Corporation, Tokyo (JP); National Institute for Materials Science, Tsukuba-Shi (JP)

( * ) Notice: Subject to any disclaimer, the term of this patent is extended or adjusted under 35 U.S.C. 154(b) by 0 days.

(21) Appl. No.: 13/704,670

(22) PCT Filed: Jun. 22, 2011

(86) PCT No.: PCT/JP2011/064861
§ 371 (c)(1),
(2), (4) Date: Dec. 17, 2012

(87) PCT Pub. No.: WO2011/162411
PCT Pub. Date: Dec. 29, 2011

(65) Prior Publication Data
US 2013/0087705 A1  Apr. 11, 2013

(30) Foreign Application Priority Data
Jun. 25, 2010 (JP) .................................. 2010-145314

(51) Int. Cl.
G01N 23/225  (2006.01)
(52) U.S. Cl.
CPC .................................. G01N 23/225 (2013.01)
USPC ............................ 250/306; 250/307; 250/310
(58) Field of Classification Search
USPC ......................................... 250/306, 307, 310
See application file for complete search history.

(56) References Cited

U.S. PATENT DOCUMENTS 6,399,944 B1  6/2002  Vasilyev et al.
8,269,167 B2 *  9/2012  deCecco et al. ............. 250/305

FOREIGN PATENT DOCUMENTS

| JP | 63-009807 A | 1/1988 |
| JP | 05-093618 A | 4/1993 |
| JP | 2002-131036 A | 5/2002 |
| JP | 2003-504609 A | 2/2003 |
| JP | 2010-043987 A | 2/2010 |

OTHER PUBLICATIONS

Hiroki Hibino et al., "Dependence of Electronic Properties of Epitaxial Few-Layer Graphene on the Number of Layers Investigated by Photoelectron Emission Microscopy", Physical Review B, Mar. 2009, pp. 125437.1-125437.7, vol. 79, No. 12.
Hiroki Hibino et al., "Analysis of No. Of Layers in Epitaxial Few-Layer Graphene Grown on SiC Towards Single-Crystal Graphene Substrate", Journal of the Vacuum Society of Japan, Feb. 2010, pp. 101-108, vol. 53, No. 2.

(Continued)

Primary Examiner — Kiet T Nguyen
(74) Attorney, Agent, or Firm — Sughrue Mion, PLLC

(57) ABSTRACT

Provided is a versatile method of determining the number of layers of a two-dimensional atomic layer thin film as compared with conventional methods. An electron beam is radiated to a two-dimensional thin film atomic structure having an unknown number of layers to determine the number of layers based on an intensity of reflected electrons or secondary electrons generated thereby. In particular, this method is effective for determining the number of layers of graphene.

14 Claims, 12 Drawing Sheets

(56) References Cited

OTHER PUBLICATIONS

Z.H. Ni et al., "Graphene Thickness Determination Using Reflection and Contrast Spectroscopy", Nano Letters, Jul. 26, 2007, pp. 2758-2763, vol. 7, No. 9.

P.E. Gaskell et al., "Counting Graphene Layers on Glass Via Optical Reflection Microscopy", Applied Physics Letters, Apr. 6, 2009, pp. 143101.1-143101.3, vol. 94, No. 14.

P. Blake et al., "Making Graphene Visible", Applied Physics Letters, 2007, pp. 063124-1-063124-3, vol. 91.

Hidefumi Hiura et al., "Determination of the Numbre of Graphene Layers: Discrete Distribution of the Secondary Electron Intensity Stemming from Individual Graphene Layers", Applied Physics Express, Sep. 25, 2010, pp. 095101.1-095101.3, vol. 3, No. 9.

A. C. Ferrai et al., "Raman Spectrum of Graphene and Graphene Layers", Physical Review Letters, 2006, pp. 187401-1-187401-4, vol. 97.

Thomas W. Ebbesen et al., "Graphene in 3-Dimensions: Towards Graphite Origami", Advanced Materials, 1995, pp. 582-586, vol. 7, No. 6.

H. Hiura et al, "Role of $sp^3$ Defect Structures in Graphite and Carbon Nanotubes", Letters to Nature, Jan. 1994, pp. 148-151, vol. 367.

Tsuneya Ando "The Electronic Properties of Graphene and Carbon Nanotubes", NPG Asia Materials, 2009, pp. 17-21, vol. 1.

* cited by examiner

METHOD FOR DETERMINING NUMBER OF LAYERS OF TWO-DIMENSIONAL THIN FILM ATOMIC STRUCTURE AND DEVICE FOR DETERMINING NUMBER OF LAYERS OF TWO-DIMENSIONAL THIN FILM ATOMIC STRUCTURE

CROSS REFERENCE TO RELATED APPLICATIONS

This application is a National Stage of International Application No. PCT/JP2011/064861 filed Jun. 22, 2011, claiming priority based on Japanese Patent Application No. 2010-145314 filed Jun. 25, 2010, the contents of all of which are incorporated herein by reference in their entirety.

BACKGROUND ART

This invention relates to a method and a device for determining the number of layers of a two-dimensional atomic layer thin film, and more particularly, to a method of determining the number of layers of a two-dimensional atomic layer thin film which is applicable to the next generation of electronics, optoelectronics, and spintronics because of exceptional electronic properties and optical characteristics and excellent mechanical characteristics and chemical characteristics.

In recent years, a material limit and a physical limit of silicon have been pointed out in the semiconductor industry. Therefore, a new semiconductor material substituting for silicon and an element structure based on a new concept are demanded.

Two-dimensional atomic layer thin films having an extremely small thickness, in particular, graphene is a new semiconductor material having a high potential to respond to the above-mentioned demand. By using excellent physical properties thereof, there is a possibility of realizing a new element which overwhelms the performance of existing elements.

The two-dimensional atomic layer thin film denotes crystal in which atoms are stably arranged on a two-dimensional plane and crystal formed by laminating the above-mentioned crystal to a thickness in the order of nanometer.

As a representative two-dimensional atomic layer thin film, graphene is first given. Graphene is a single layer extracted from graphite which is a layered material consisting of $sp^2$-hybridized carbon alone and is an extremely stable monoatomic layer planar material.

Graphene has the structure of a honeycomb-like quasi-two-dimensional sheet in which six-carbon rings, each having a regular hexagonal shape having carbon atoms at vertices, are arranged without any gap. A distance between carbon atoms is about 1.42 angstroms ($1.42 \times 10^{-10}$ m), and a layer thickness is 3.3 to 3.4 angstroms (3.3 to $3.4 \times 10^{-10}$ m) in the case where an underlayer is graphite and is about 10 angstroms ($10 \times 10^{-10}$ m) on other substrates.

As the size of the graphene plane, various sizes varying from a molecular size with a length of one side in the order of nanometer to theoretically an infinite size can be supposed. In general, graphene denotes a single layer of graphite. However, graphene often has two or more layers as the number of layers. In such a case, graphene having one layer, two layers, and three layers are respectively referred to as monolayer graphene, bilayer graphene, and trilayer graphene. Graphene having the number of layers up to about 10 is collectively referred to as few-layer graphene. Moreover, graphene other than the monolayer graphene is referred to as multilayer graphene.

As described in "The electronic properties of graphene and carbon nanotubus" by Ando, NPG asia materials 1(1), 2009, pp. 17 to 21 (Non Patent Literature 1), an electronic state of graphene can be expressed by the Dirac equation in a low-energy region. This point contrasts strongly with an electronic state of substances other than graphene which can be well expressed by the Schrodinger equation.

An electron energy of graphene has a linear dispersion relationship with respect to a wavenumber in the vicinity of a K point, more specifically, can be expressed by two straight lines respectively having positive and negative gradients corresponding to a conduction band and a valence band. A point of intersection of the straight lines is referred to as the Dirac point at which graphene electrons have peculiar electronic physical properties of behaving as fermion having an effective mass equal to zero. Because of the above-mentioned electronic properties, graphene has a feature of exhibiting the highest mobility of $10^6$ cm$^2$V$^{-1}$s$^{-1}$ or higher among existing materials and a small temperature dependence.

The monolayer graphene is basically a metal or a semi-metal having zero band gap. When the size is in the order of nanometer, however, the band gap becomes greater. As a result, the monolayer graphene becomes a semiconductor having a finite band gap depending on a width and an edge structure of graphene. Moreover, the bilayer graphene has zero band gap without perturbation. However, when perturbation which destroys the minor symmetry between the two graphene layers, for example, an electric field is applied, the bilayer graphene has a finite gap in accordance with the magnitude of the electric field.

For example, with the electric field at 3 Vnm$^{-1}$, a gap becomes about 0.25 eV. In the case of the trilayer graphene, semi-metallic electronic properties, in which the conduction band and the valence band overlap each other over a width of about 30 meV, are exhibited. In terms of the overlap of the conduction band and the valence band, the trilayer graphite is close to bulk graphite. The graphite having four or more layers also exhibits the semi-metallic electronic properties. With an increase in the number of layers, the electronic properties of graphene gradually become closer to those of bulk graphite.

Moreover, graphene is also excellent in mechanical characteristics. One layer of graphene has a remarkably large Young's modulus as large as 2 TPa (terapascal). A tensile strength is at the highest level among the existing materials.

In addition, graphene has a unique optical characteristic. For example, in a wide electromagnetic-wave region ranging from a ultraviolet region (wavelength: up to 200 nm) to a region in the vicinity of terahertz light (wavelength: up to 300 μm), a transmissivity of graphene is 1−nα (n: number of layers of graphene, n=about 1 to 10, α: fine-structure constant, $\alpha = e^2/2hc\epsilon_0 = 0.0229253012$, e: elementary charge, h: Planck's constant, $\epsilon_0$: permittivity of vacuum), specifically, is represented not by a material constant of graphene but only by fundamental physical constants. This is a characteristic unique to graphene, which cannot be seen for other substances and materials.

Further, the transmissivity and a reflectance of graphene exhibit carrier-density dependence in the terahertz light region. This fact means that the optical characteristics of graphene can be controlled based on a field effect. It is known that other two-dimensional atomic layer thin films also have peculiar physical properties based on dimensionality.

As described above, because of the exceptional electronic properties and optical characteristics and excellent mechanical characteristics and chemical characteristics, graphene is expected to be used in a wide range of industrial field from chemicals to electronics. In particular, the use of graphene for semiconductor devices and micromechanical devices in the fields of electronics, spintronics, optoelectronics, micro/nanomechanics, and bioelectronics of the next generation has been expanded around the world. Similarly to graphene, other two-dimensional atomic layer thin films are also actively studied and developed for industrial use.

In the industrial use of the two-dimensional atomic layer thin films, a method of determining the number of layers is extremely important. This is because the electronic properties and optical characteristics of graphene remarkably change depending on the number of layers. Therefore, for the demonstration of a desired function, a device is required to be manufactured after the number of layers of graphene is previously determined.

Currently, as a method of determining the number of layers of graphene, the following three types of methods are known. That is, there are known a method employing an optical microscope described in P. Blake et al., "Making graphene visible", Applied Physics Letters, vol 91, 2007, 063124-1-3 (Non Patent Literature 2), a method employing a surface-probe microscope such as an atomic force microscope (AFM) and a scanning tunneling microscope (STM) described in H. Hiura, T. W. Ebbesen, J. Fujita, K. Tanigaki and T. Takada, "Role of $sp^3$ defect structures in graphite and carbon nanotubes", Letters to nature, January 1994, vol 367, p. 148-151 (Non Patent Literature 3) and Thomas W. Ebbesen and Hidefumi Hiura, "Graphene in 3-Dimensions: Towards Graphite Origami", Advanced Materials, vol 7, No 6, 1995, p. 582-586 (Non Patent Literature 4), and a method employing Raman spectrum described in A. C. Ferrai et al., "Raman Spectrum of Graphene and Graphene layers", Physical Review Letters, vol 97, 2006, p. 187401-1-4 (Non Patent Literature 5).

The method of determining the number of layers of graphene using the optical microscope is based on the principle that, in graphene present on a silicon (Si) substrate covered with silicon oxide ($SiO_2$), there occurs of a change (about 1.5% or larger) visually verifiable by the naked eye in contrast between an $SiO_2$ surface and graphene due to a shift of an interference effect of optically reflected light at an $SiO_2$/Si interface and the $SiO_2$ surface in accordance with the number of layers of graphene. In this case, a thickness of the $SiO_2$ film is limited to 90 nm or 300 nm at which the interference effect between incident light and the reflected light from the Si interface is present. A procedure of the above-mentioned method is as follows. First, graphene is applied onto the $SiO_2$/Si substrate by an appropriate method. Next, an optical-microscope image of graphene is obtained. Finally, a contrast ratio of the $SiO_2$ surface and that of the optical-microscope image of graphene are compared. For example, a gradation of the $SiO_2$ surface is normalized and is regarded as 100%. Then, when a thickness of an oxide film is 90 nm, the normalized gradation of the graphene portion is reduced by about 6.45% as the number of layers increases one by one. When the thickness of the oxide film is 300 nm, the amount of reduction slightly increases. For example, the gradation is reduced to about 93.55% for the monolayer graphene, about 87.10% for the bilayer graphene, about 80.65% for the trilayer graphene, about 74.20% for four-layer graphene, about 67.75% for five-layer graphene, and about 61.30% for six-layer graphene. In this manner, the number of layers can be optically determined up to about six layers.

With the method using the surface-probe microscope, an absolute distance in a height direction of graphene applied onto an appropriate substrate is measured with a high spatial resolution of the AFM. When n is the number of layers, a thickness t of graphene measured by the AFM is expressed by: $t=t_0+0.34\times(n-1)$ [nm]. Although $t_0$ corresponds to the thickness of monolayer graphite, $t_0$ is a constant different for each type of substrate. For example, when the substrate is made of $SiO_2$, $t_0\approx1$ [nm]. The method of determining the number of layers with the STM is almost the same as that with the AFM. In the case with the STM, however, the substrate, on which graphene is placed, is limited to a conductive one.

In the determination of the number of layers with the Raman spectrum, the number of layers of graphene is determined based on a relative intensity ratio of a G band and a 2D band (also referred to as "G' band") of graphene, a wavenumber (energy) of the 2D band, and a shape of the 2D band.

DISCLOSURE OF THE INVENTION

However, the above-mentioned methods of determining the number of layers of graphene have the following problems.

First, the method of determining the number of layers of graphene using the optical microscope has the following problems.

(1) Restrictions on Usable Substrates:

In the case of the method of determining the number of layers of graphene using the optical microscope, the usable substrate is only one type, that is, an Si substrate with an oxide film. Further, a thickness of the oxide film is limited to any one of 90 nm and 300 nm. The limitation is due to the use of the optical interference effect to determine the number of layers. Specifically, in order to visually verify the optical interference effect by the naked eye, the contrast ratio is required to be about 1.5% or higher. The limitation of the type of substrate to be used only to the specific Si substrate becomes a heavy drag on the application of graphene. For example, the fact that the substrate cannot be selected for manufacturing the graphene device causes the range of application of the graphene device to be remarkably narrowed.

(2) Restrictions on Size of Graphene for Which the Number of Layers Can Be Determined:

In the case of the method of determining the number of layers of graphene using the optical microscope, the number of layers of graphene having size equal to or smaller than about 500 nm cannot be determined. This is because visible light is used for the measurement of graphene. Therefore, graphene having the size equal to or smaller than about a wavelength of visible light (about 500 nm) cannot be identified due to diffraction limitation. This fact means that the number of layers of graphene or a graphene device, which is finely processed in the order of submicron or smaller, cannot be determined. As described above, graphene has totally different electronic properties depending on the number of layers. Therefore, the inability of knowing the number of layers of finely processed graphene remarkably limits the application of graphene to the device.

(3) Restrictions on a Determinable Number of Layers:

With the method of determining the number of layers of graphene using the optical microscope, a determinable number of layers is only about up to six. The reason is that a linearity between the number of layers of graphene and the contrast ratio is kept only for 1 to about 6 layers. As described above, in the above-mentioned method, the number of layers is determined by using the reduction of the contrast ratio with underlying $SiO_2$ at a given constant rate as the number of layers of graphene increases. The linearity is kept up to about six layers of graphene. When the number of layers is greater than six, a nonlinearity appears. Therefore, it becomes difficult to reliably determine the number of layers.

On the other hand, the method using the surface-probe microscope has the following problems.

(1) Measurement Accuracy:

The method using the surface-probe microscope has a problem in that ambiguity and uncertainty remain in the determination of the number of layers. The problem is caused due to, as described above, the thickness t of graphene measured by the AFM being expressed by: $t_0+0.34\times(n-1)$ [nm] (n: number of layers, $t_0$: constant different for each substrate). The constant $t_0$ reflects a difference in an atomic force between the substrate and graphene, specifically, a difference between a friction coefficient of an AFM chip with respect to the substrate and that with respect to graphene, and therefore also depends on a shape and a material of the AFM chip. Specifically, $t_0$ differs for each measurement system. Therefore, ambiguity always remains in the measurement of $t_0$. Moreover, a proportional of the above-mentioned expression is established under the premise that a response of a piezoelement for driving the AFM is linear. However, the precondition is not always satisfied. Even with calibration, work for satisfying the precondition becomes extremely troublesome, and therefore is not practical. For the reasons described above, the number n of layers obtained by back calculation using the above-mentioned expression contains accumulated incertitude.

(2) Practicality:

With the method using the surface-probe microscope, the surface-probe microscope has limitative general use in the industry, and therefore has little practicality. This is due to disadvantages in that the range of measurement is narrow and a measurement time is long. Another reason lies in a disadvantage in the difficulty in the application of the scanning probe microscope to a surface substrate which is greatly undulating. This is because the measurement is performed so that the probe traces the surface while feedback is applied to the piezoelement. Therefore, in the industry, the use of the surface-probe microscope for the determination of the number of layers of graphene is not practical.

Further, the method of determining the number of layers of graphene using the Raman spectrum has the following problems.

(1) Restrictions on the Determinable Number of Layers:

The number of layers, which can be determined with the method of determining the number of layers of graphene using the Raman spectrum, is smaller than five. The reason is because a position and a shape of a Raman band which characterizes graphene having each number of layers irregularly change as the number of layers increases.

(2) The Method Resulting in Destructive Inspection:

With the method of determining the number of layers of graphene using the Raman spectrum, high-density laser radiation is performed. Therefore, graphene is non-crystallized to remarkably deteriorate the characteristics of graphene. The reason is because a laser beam is inevitably required to be condensed so as to obtain a Raman spectrum of extremely small graphene in the order of micrometer. Even with the energy of 1 mW or smaller, if the laser beam is focused to the same level as a wavelength, graphene becomes amorphous carbon. Therefore, the method of determining the number of layers of graphene using the Raman spectrum inevitably becomes a destructive inspection.

As described above, the above-mentioned three methods all have shortcomings, and therefore a versatile method of determining the number of layers of graphene to overcome the shortcomings is desired. Moreover, a method of evaluating the number of layers of two-dimensional atomic layer thin films other than graphene is not known. Currently, the development of the evaluation method is waited for.

This invention has been made in view of the problems described above, and therefore has an object to provide a versatile method of determining the number of layers of a two-dimensional atomic layer thin film as compared with conventional methods.

In order to solve the above-mentioned problems, according to a first exemplary embodiment of this invention, there is provided a method of determining a number of layers of a two-dimensional thin film atomic structure, the method including radiating an electron beam to the two-dimensional thin film atomic structure having an unknown number of layers to determine the number of layers based on an intensity of reflected electrons or secondary electrons generated thereby.

According to a second exemplary embodiment of this invention, there is provided a layer-number determining device for a two-dimensional thin film atomic structure, the layer-number determining device including a layer-number determining mechanism for radiating an electron beam to the two-dimensional thin film atomic structure having an unknown number of layers to determine the number of layers based on an intensity of reflected electrons or secondary electrons generated thereby.

Effect of the Invention

According to this invention, it is possible to provide a versatile method of determining the number of layers of a two-dimensional atomic layer thin film as compared with conventional methods.

Figure 1:
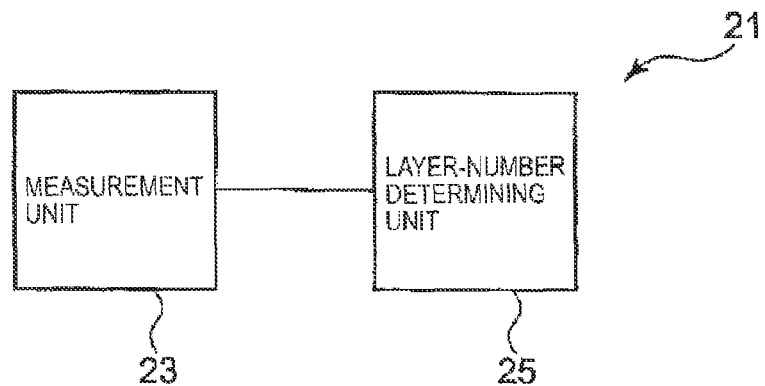
FIG. 1 is a block diagram illustrating a schema of a layer-number determining device.

REFERENCE SIGNS LIST 1 substrate
2 graphene
3 primary electron beam
4 substrate surface-layer interior when secondary electrons are generated
5 secondary electrons which do not pass through graphene
6 secondary electrons which passed through graphene having single layer
7 secondary electrons which passed through graphene having two layers
8 secondary electrons which passed through graphene having three layers
9 secondary electrons which passed through graphene having four layers
10 process of generation of secondary electrons without graphene
11 process of generation of secondary electrons when graphene has single layer
12 process of generation of secondary electrons when graphene has two layers
13 process of generation of secondary electrons when graphene has three layers
14 process of generation of secondary electrons when graphene has four layers
15 portion at which intensity of secondary electrons attenuates when graphene has single layer
16 portion at which intensity of secondary electrons attenuates when graphene has two layers
17 portion at which intensity of secondary electrons attenuates when graphene has three layers
18 portion at which intensity of secondary electrons attenuates when graphene has four layers
19 cable
21 layer-number determining device
23 measurement unit
25 layer-number determining unit
31 radiation section
33 detection section
35 external connection section
37 bus
41 external connection section
43 control section
45 storage section
47 input section
48 output section
49 layer-number determination program
50 bus
51 calibration-curve data

BEST MODE FOR EMBODYING THE INVENTION

In the following, a preferred embodiment of this invention is described in detail based on the drawings.

First, a configuration of a layer-number determining device 21 according to this embodiment is described referring to FIGS. 1 to 4.

As illustrated in FIG. 1, the layer-number determining device 21 includes a measurement unit 23 for radiating an electron beam to a two-dimensional atomic layer thin film to measure an intensity of reflected electrons or secondary electrons generated thereby, and a layer-number determining unit 25 for determining the number of layers of the two-dimensional atomic layer thin film based on the intensity of the secondary electrons, measured by the measurement unit 23. The measurement unit 23 and the layer-number determining unit 25 constitute a layer-number determining mechanism.

Figure 2:
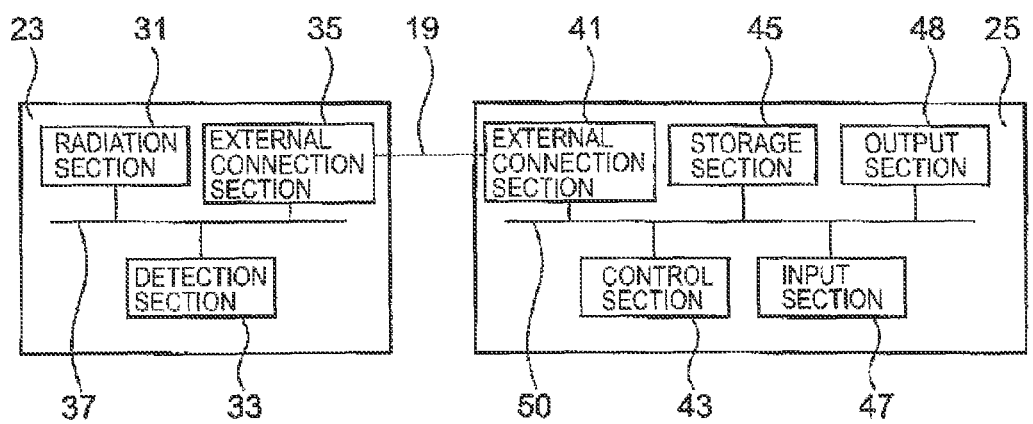
FIG. 2 is a detail view of FIG. 1.

The measurement unit 23 is, for example, a scanning electron microscope (SEM), and includes, as illustrated in FIG. 2, a radiation section 31 for radiating the electron beam, a detection section 33 for detecting the reflected electrons or the secondary electrons to acquire an electron image, and an external connection section 35 for connecting the measurement unit 23 to the exterior. The radiation section 31, the detection section 33, and the external connection section 35 are connected by a bus 37 or the like.

The layer-number determining unit 25 is, for example, a computer, and includes an external connection section 41 for connecting the layer-number determining unit 25 to the exterior through a cable 19 or the like, a control section 43 including a CPU, a ROM, a RAM, and the like for controlling the driving of each component, a storage section 45 including a program for operating each of the components, an input section 47 such as a mouse or a keyboard, for inputting measurement conditions or the like, and an output section 48 for outputting a measurement result. The components are connected by a bus 50.

Figure 3:
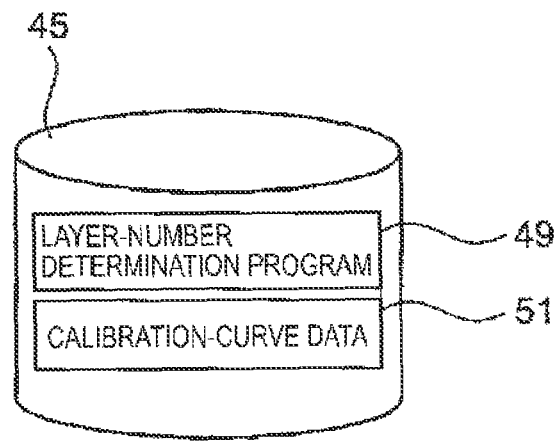
FIG. 3 is a view illustrating a storage section of FIG. 2.

As illustrated in FIG. 3, the storage section 45 includes a layer-number determination program 49 for operating the layer-number determining device 21 and calibration-curve data 51 which is data of a calibration curve to be used to determine the number of layers.

Figure 4:
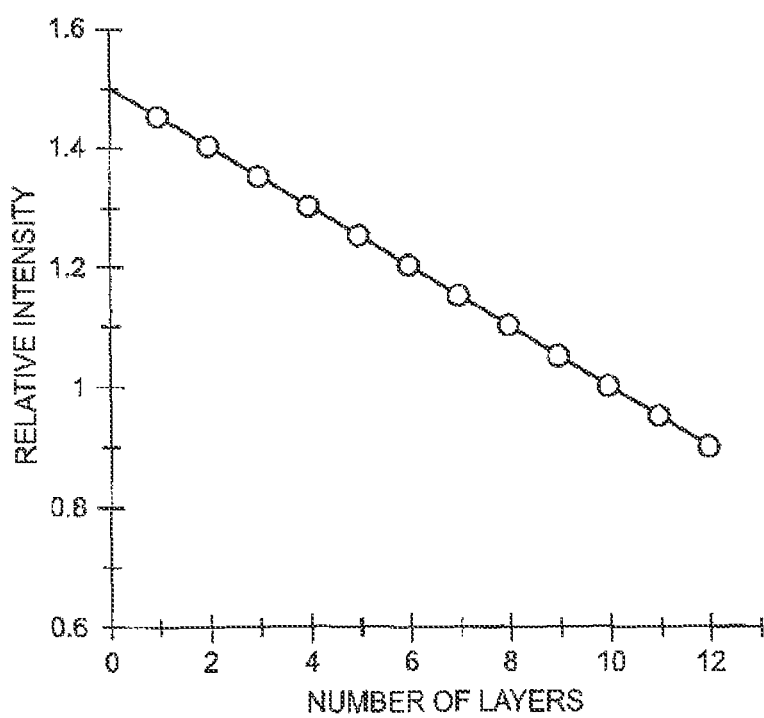
FIG. 4 is a schematic diagram of calibration-curve data.

As illustrated in FIG. 4, the calibration-curve data 51 is data indicating the relationship between the intensity of the reflected electrons or the secondary electrons (here, a relative intensity to a substrate) and the number of layers and has a linear relationship as illustrated in FIG. 4. As described below, the linear relationship is obtained only when the electron beam is radiated under specific conditions (in particular, an accelerating voltage).

Next, a method of determining the number of layers of the two-dimensional atomic layer thin film using the layer-number determining device 21 is described referring to FIGS. 5 to 13.

Graphene is described here as an example of the two-dimensional atomic layer thin film.

Figure 5:
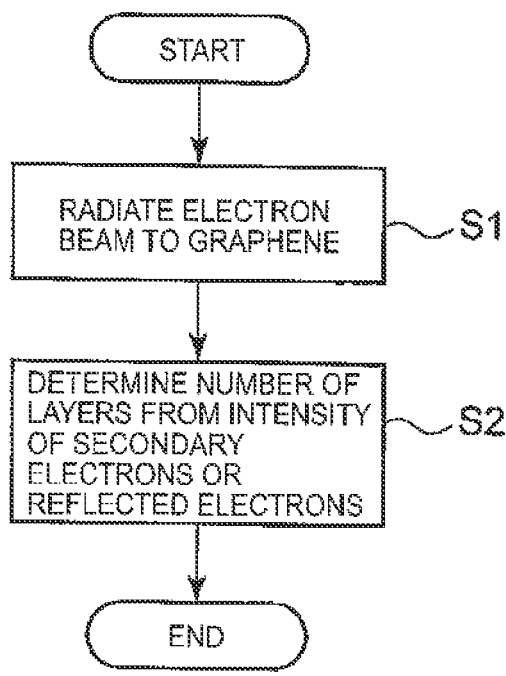
FIG. 5 is a flowchart illustrating a schema of a method of determining the number of layers.

First, a schema of the method of determining the number of layers is described referring to FIG. 5.

As illustrated in FIG. 5, the layer-number determining device 21 uses the measurement unit 23 to radiate an electron beam (primary electrons) to graphene having an unknown number of layers (S1).

Next, as illustrated in FIG. 5, the layer-number determining device 21 uses the layer-number determining unit 25 to determine the number of layers of graphene having the unknown number of layers based on the intensity of the reflected electrons or the secondary electrons generated by the radiation of the electron beam (S2).

Next, the details of the method of determining the number of layers are described referring to FIGS. 6 to 13.

Figure 6:
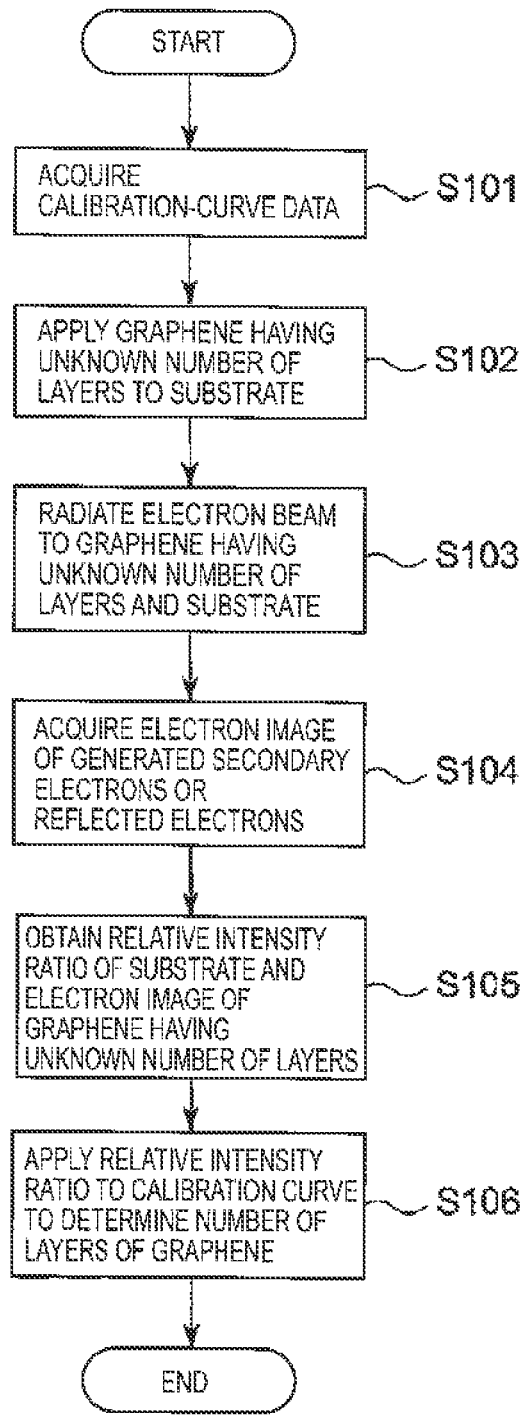
FIG. 6 is a flowchart illustrating the details of the method of determining the number of layers.

First, as illustrated in FIG. 6, the control section 43 activates the layer-number determination program 49 stored in the storage section 45 to acquire the calibration-curve data 51 of graphene (S101, a method of acquiring the calibration-curve data 51 is described later).

Figure 7:
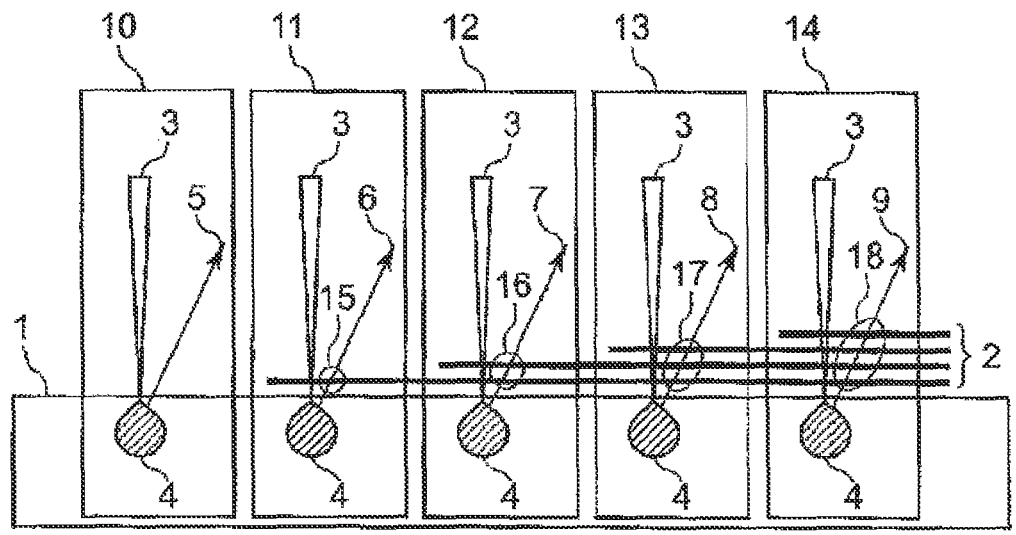
FIG. 7 is a schematic view for illustrating the reason of appearance of a linear relationship between a secondary-electron intensity on an SEM image of graphene and the number of layers of graphene.

Now, the reason why the calibration-curve data 51 has the linearity as shown in FIG. 4 is described referring to FIG. 7.

In FIG. 7, the reference symbol 1 denotes a substrate and the reference symbol 2 denotes graphene. The reference symbol 10 denotes a process of the generation of the secondary electrons without graphene, whereas the reference symbols 11, 12, 13, and 14 respectively indicate processes of the generation of the secondary electrons when graphene has a single layer, two layers, three layers, and four layers. As described above for S1, when a (primary) electron beam 3 is radiated to the substrate 1, primary electrons repeatedly collide against each other in a substrate surface-layer interior 4 to generate secondary electrons. A part thereof leave the substrate 1 to become secondary electrons 5, 6, 7, 8, and 9 to reach a detector (not shown) of the detection section 33 where the number of secondary electrons is counted. A kinetic energy of the primary electrons is about 1,000 eV (electron volt), and therefore is large as compared with a kinetic energy of the secondary electrons (several eV). Therefore, the primary electrons reach the substrate surface-layer interior 4 while being little affected by the shield by graphene. On the other hand, the kinetic energy of the secondary electrons is several eV as described above, and therefore is smaller than the kinetic energy of the primary electrons. Therefore, a shielding effect provided by graphene is great. Accordingly, the intensity of the secondary electrons attenuates as the secondary electrons pass through graphene. Portions at which the intensity of the secondary electrons attenuates are indicated by the reference symbols 15, 16, 17, and 18 for the single layer, the two layers, the three layers, and the four layers of graphene, respectively. The attenuation increases as the number of layers increases. The relationship described above is expressed as the following formula. First, for simplification, the intensity of the secondary electrons 5 in the case 10 without graphene is normalized to 1. An ability of generating the secondary electrons of the graphene 2 and that of the substrate 1 generally differ from each other. Therefore, let a ratio of the ability of generating the secondary electrons of the graphene 2 and that of the substrate 1 be $\alpha$. Then, it is considered that the above-mentioned attenuation amount generated with the passage through graphene is proportional to the number of layers of graphene. Therefore, when the attenuation amount is $\Delta$, the intensities of the secondary electrons 6, 7, 8, and 9 in the case 11 where graphene has the single layer, the case 12 where graphene has two layers, the case 13 where graphene has three layers, and the case 14 where graphene has four layers are respectively $\alpha-1\Delta$, $\alpha-2\Delta$, $\alpha-3\Delta$, and $\alpha-4\Delta4$. When the number of layers of graphene is n, the secondary-electron intensity is $\alpha-n\Delta$ (n is a natural number). This relationship describes the reason why the linearity appears between the secondary-electron intensity on the SEM image of graphene and the number of layers of graphene.

In the case where the calibration-curve data 51 is already acquired, S101 is not required.

Next, as illustrated in FIG. 6, graphene having the unknown number of layers, that is, graphene for which the number of layers is desired to be determined, is placed on the substrate (S102).

Graphene can be obtained by, for example, being peeled off thinly from natural graphite with a pressure-sensitive adhesive tape. As a material of the graphene, there may be used, in addition to the above-mentioned natural graphite, highly oriented pyrolytic graphite (HOPG), Kish graphite, chemical vapor deposition (CVD) graphene, and epitaxial graphite obtained by causing silicon carbide (SiC) to thermally decompose.

In addition, as the substrate, there may be used an Si substrate, a semiconductor substrate made of gallium arsenide (GaAs) or the like, an insulator substrate made of sapphire, mica, glass, or the like, a plastic substrate made of polyimide, fluororesin, polyethylene, or the like, and a metal substrate made of copper, steel, aluminum, or the like. It is desirable to previously clean the substrate, for example, by washing or with an oxygen plasma so as not to disturb the observation. In the case of CVD graphene and epitaxial graphite obtained by causing SiC to thermally decompose, the substrate obtained by growth can be directly used without a process of mechanical stripping and application to the substrate.

Next, the control section 43 directs the radiation of the electron beam to the substrate and graphene placed on the substrate under predetermined conditions based on the layer-number determination program 49 so that the radiation section 31 radiates the electron beam (S103, (a), an electron-image acquiring section).

At this time, a secondary-electron accelerating voltage affects the intensity of the reflected electrons or the secondary electrons. Therefore, the accelerating voltage is selected from the range which allows the linear relationship to be obtained between the number of layers of graphene and the reflected electrons or the secondary electrons as in the case of the calibration-curve data 51.

Figure 8:
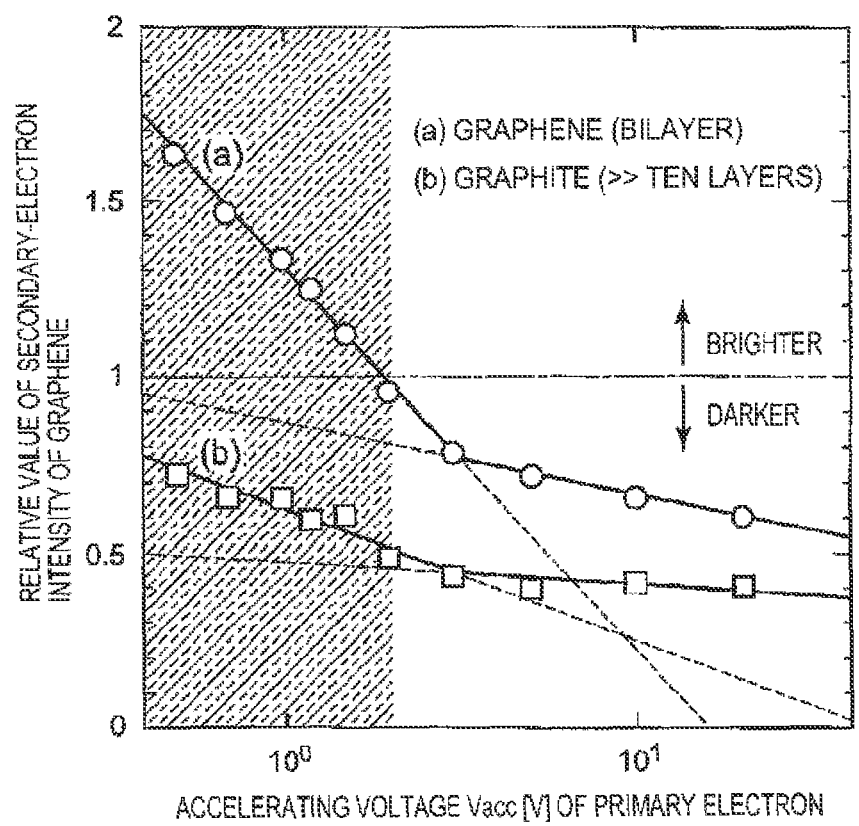
FIG. 8 is a graph showing a primary-electron accelerating voltage dependence of SEM images of graphene and graphite.

As an example, a primary-electron accelerating voltage dependency of the SEM images of graphene and graphite are shown in FIG. 8 as a graph. The vertical axis of FIG. 8 indicates a relative secondary-electron intensity on the SEM images of a graphene piece (two layers) and a graphite piece (>>ten layers) with respect to underlying $SiO_2$, whereas the horizontal axis indicates the accelerating voltage ($V_{acc}$) of the primary electrons used for the observation with the SEM. The secondary-electron intensity of graphene or the like is divided by the intensity of the secondary electrons at the substrate surface to be normalized as a relative value. In this manner, the effects of an instrumental function such as an absolute intensity of the primary electrons and a sensitivity characteristic of the secondary-electron detector are eliminated. As indicated by (a) in FIG. 8, when $V_{acc}$ is equal to or smaller than about 2 kV, the relative value of the secondary-electron intensity is 1 or larger for graphene (shaded area). The graphite piece has the relative value smaller than 1 at any value of $V_{acc}$ as indicated by (b). Moreover, as the accelerating voltage becomes lower, a higher relative value of the secondary-electron intensity is observed. In the above-mentioned example, only the cases where the number of layers of graphene is one and two are shown. According to another observation, in the case of $V_{acc}$<2.0 kV, graphene has a relatively high secondary-electron intensity as compared with underlying $SiO_2$ when the number of layers of graphene is up to about ten and several. When observed by the SEM, graphene is observed as being particularly bright. Therefore, in a situation where graphene and graphite are present at the same time, graphene can be identified at a glance.

An important point in the SEM image of graphene is that the secondary-electron intensity of the SEM image of graphene decreases as the number of layers of graphene increases when graphene is observed by the SEM within a specific range of the primary-electron accelerating voltage. This fact means that the number of layers of graphene can be determined, specifically, the calibration-curve data 51 as shown in FIG. 4 can be obtained by using the secondary-electron intensity of graphene as an index. Although the details are described below, the linear relationship between the secondary-electron intensity on the SEM image of graphene and the number of layers is observed, as in the case of the calibration-curve data 51 shown in FIG. 4, in the case where the primary-electron accelerating voltage in the range of $0.5 \text{ kV} < V_{acc} < 1.6 \text{ kV}$ is used when the substrate, on which graphene is placed is, for example, the Si substrate with the $SiO_2$ film, the primary-electron accelerating voltage in the range of $0.5 \text{ kV} < V_{acc} < 2.0 \text{ kV}$ is used when the substrate is a sapphire substrate, and the primary-electron accelerating voltage in the range of $0.5 \text{ kV} \le V_{acc} \le 2.0 \text{ kV}$ is used when the substrate is a mica substrate. Even with other substrates, the linear relationship is observed in the case where the accelerating voltage of the primary electrons falls approximately in the range of $0.5 \text{ kV} < V_{acc} < 2.0 \text{ kV}$. Specifically, in S103, the control section 43 controls the accelerating voltage so that $V_{acc}$ falls within the above-mentioned range.

Next, the control section 43 controls the detection section 33 to acquire a secondary-electron image or a reflected-electron image of graphene (hereinafter, abbreviated as "SEM image") (S104, (a), an electron-image acquiring section).

Figure 9:
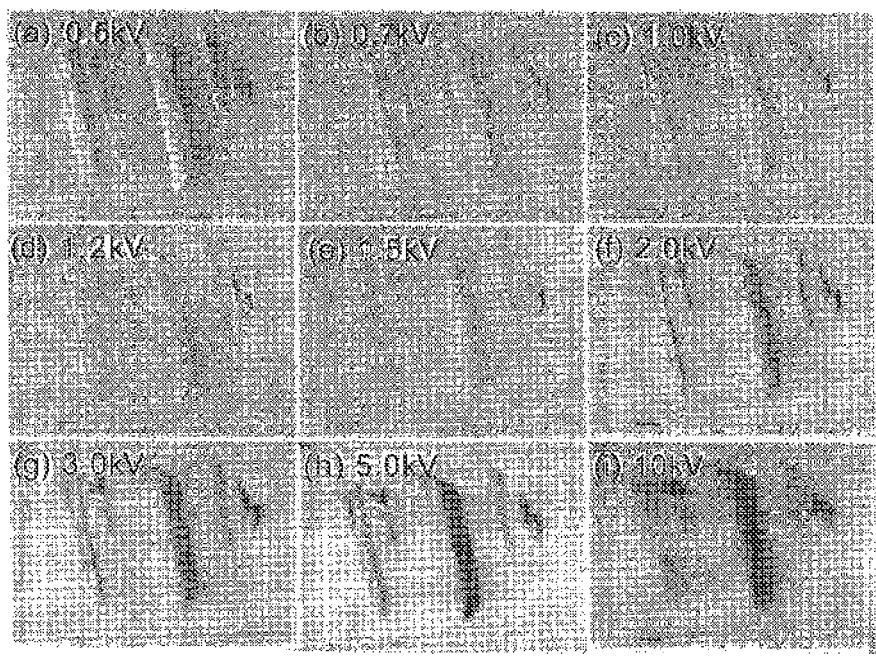
FIG. 9 are examples of views representing electron images of graphene pieces (monolayer graphene 1, monolayer graphene 2, and bilayer graphene) and graphite pieces.

FIG. 9 show examples of views representing electron images of the graphene pieces (the monolayer graphene 1, the monolayer graphene 2, and the bilayer graphene) provided on an Si substrate covered with an $SiO_2$ film having a thickness of 90 nm and the graphite piece. For reference, FIG. 10 show a view representing an optical-microscope image when the same graphene is observed with the optical microscope.

A numerical value on the upper left of each view of FIG. 9 indicates the primary-electron accelerating voltage at the time of SEM image acquisition. FIG. 9(a) corresponds to the case where $V_{acc}$=0.5 kV, FIG. 9(b) corresponds to the case where $V_{acc}$=0.7 kV, FIG. 9(c) corresponds to the case where $V_{acc}$=1.0 kV, FIG. 9(d) corresponds to the case where $V_{acc}$=1.2 kV, FIG. 9(e) corresponds to the case where $V_{acc}$=1.5 kV, FIG. 9(f) corresponds to the case where $V_{acc}$=2.0 kV, FIG. 9(g) corresponds to the case where $V_{acc}$=3.0 kV, FIG. 9(h) corresponds to the case where $V_{acc}$=5.0 kV, and FIG. 9(i) corresponds to the case where $V_{acc}$=10 kV. As is apparent from FIG. 9, a noticeable point in the SEM images (electron images) lies in that the graphene pieces are observed as being brighter than the underlying $SiO_2$ in the case where $V_{acc}$<2.0 kV, while the graphite piece is observed as being darker than the underlying $SiO_2$ with any value of $V_{acc}$. The brightness described herein indicates the intensity of the secondary electrons (including the reflected electrons; the same applies hereinafter) by the SEM.

As illustrated in FIGS. 10(a) and 10(c), based on the relationship between a relative reflected-light intensity (corresponding to the number of layers of graphene) and a relative frequency, graphene surrounded by a white dotted line on the far left in FIG. 10(b) is identified as monolayer one, whereas the second graphene from the left in FIG. 10(b), surrounded by a white dotted line, is identified as bilayer one. For the optical determination of the number of layers of graphene, the fact that the reflected-light intensity of graphene is reduced by 6.45% as the number of layers increases by one when the reflected-light intensity of the underlying $SiO_2$ is regarded as 100% is used.

Figure 10:
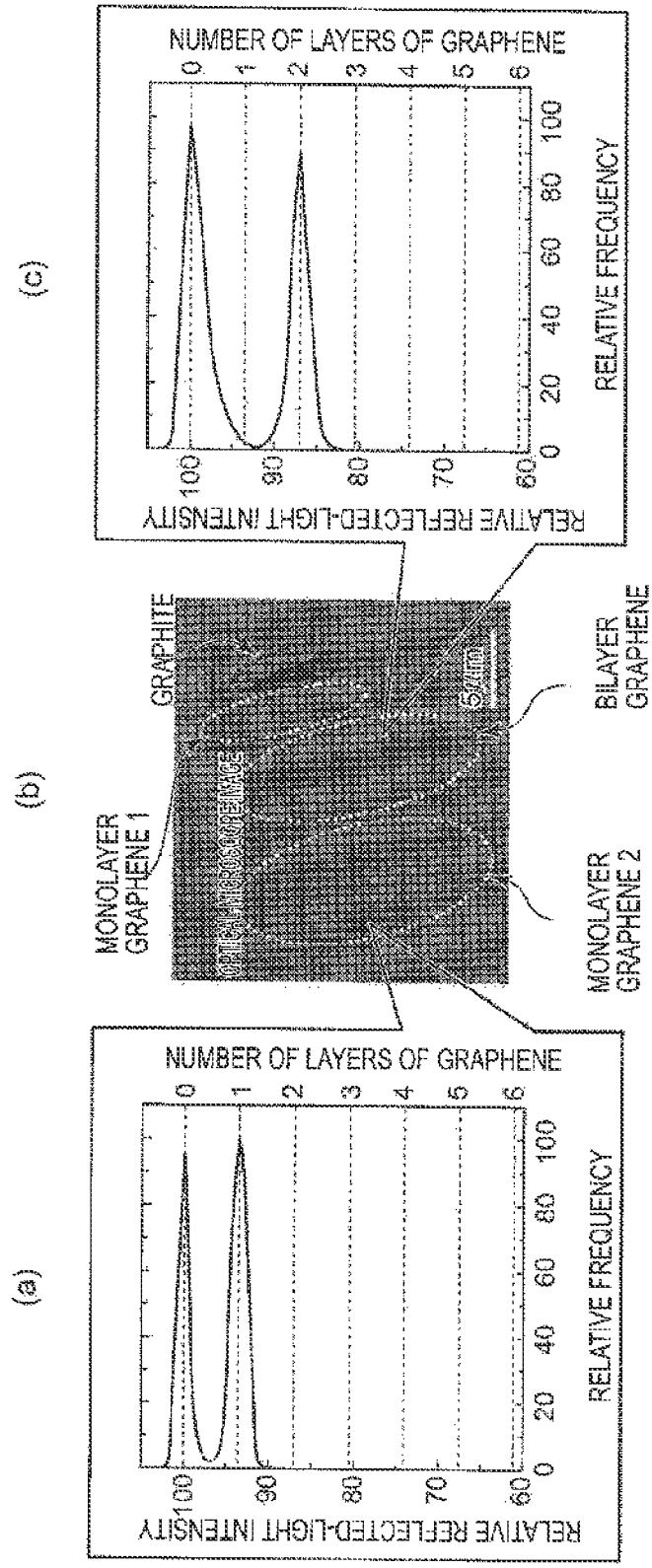
FIG. 10 are views representing optical-microscope images when the same graphene pieces as those illustrated in FIG. 9 are observed by an optical microscope.

As is apparent from FIGS. 9 and 10, in the case of the view representing the optical-microscope image of FIG. 10(b), in the vicinity of the monolayer graphene 2, only three pieces of monolayer graphene are visibly observed. In the case of the views representing the SEM images of FIGS. 9(a) to 9(f), at least five thin graphene pieces (width: 500 nm or smaller) can be observed in addition to the above-mentioned three graphene pieces. The results of observation show that graphene having a width equal to or smaller than the wavelength of light cannot be evaluated by the optical microscope due to optical limitation while graphene even in nanosize can be evaluated with the SEM. According to this invention, by performing an image analysis described below, the number of layers of graphene even in nanosize can be determined. FIG. 9 show that no damage is observed in the graphene sample even though the same graphene samples are acquired at various primary-electron acceleration voltages and therefore graphene can be evaluated in a nondestructive manner.

Next, as illustrated in FIG. 6, a relative intensity ratio of the substrate and the electron image of graphene having the unknown number of layers is obtained (S105, (b), an intensity-ratio analysis section).

Specifically, the secondary-electron intensity of graphene is divided by the secondary-electron intensity at the substrate surface to be normalized as a relative value. In this manner, the relative intensity ratio of the electron image of graphene is obtained.

As described above, by using the relative intensity ratio, the effects of the instrumental function such as the absolute intensity of the primary electrons and the sensitivity characteristic of the secondary-electron detector can be eliminated.

Next, as illustrated in FIG. 6, the relative intensity ratio is applied to the calibration curve to determine the number of layers of graphene (S106, (c), the layer-number determining section).

Specifically, the number of layers corresponding to the relative intensity ratio on a graph line of the calibration-curve data 51 shown in FIG. 4 is obtained as the number of layers of graphene.

The method of determining the number of layers is as described above.

Figure 11:
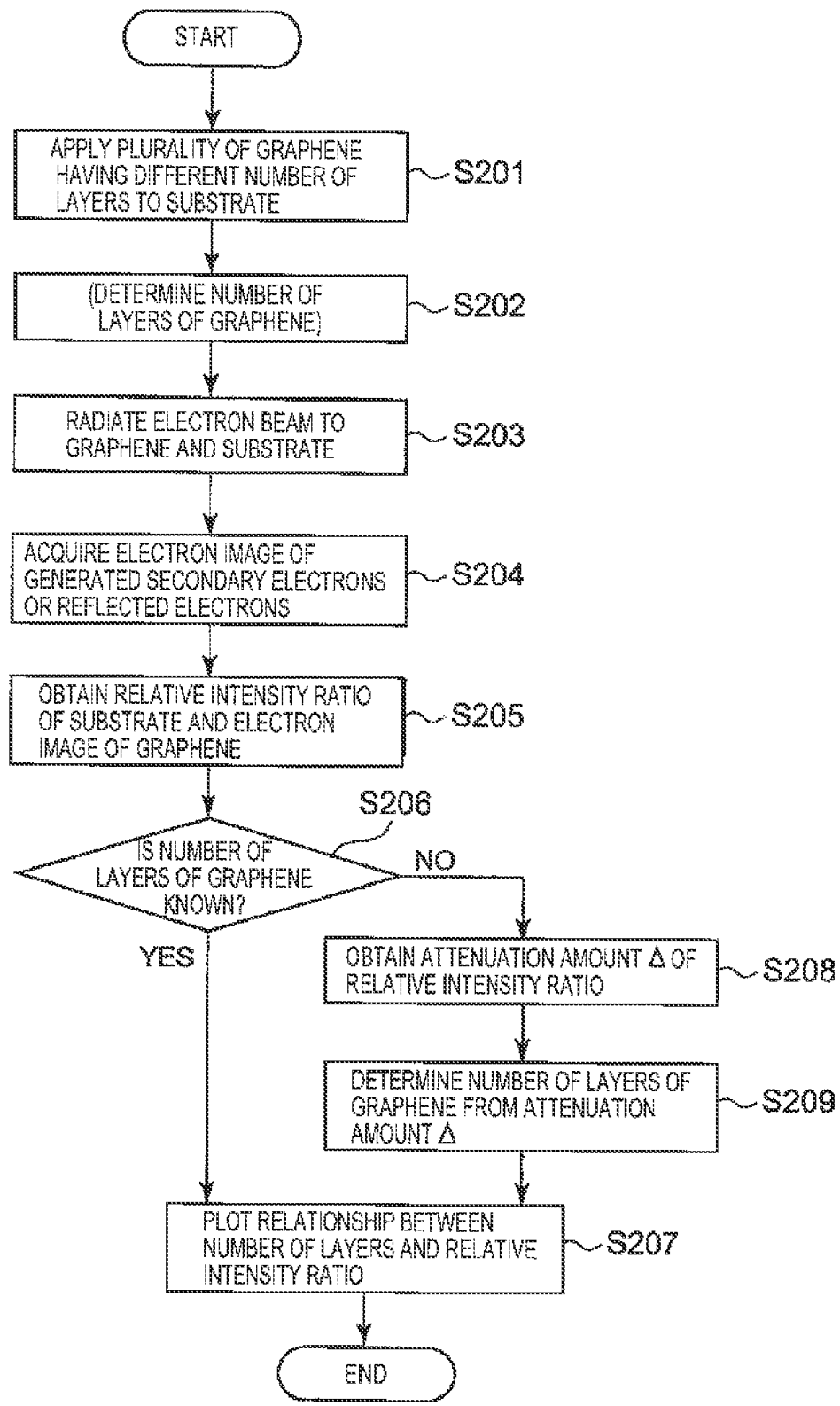
FIG. 11 is a flowchart illustrating a method of acquiring the calibration-curve data.

Now, a method of acquiring the calibration-curve data 51 in S101 is described referring to FIG. 11.

First, a plurality of graphene, each having a different number of layers, are prepared and are applied onto the substrate (S201). As the substrate, a substrate made of the same material as that of the substrate onto which graphene having the unknown number of layers is applied is used.

Next, if possible, the number of layers of each graphene is determined by the optical measurement, the Raman measurement, the AFM measurement, or the like (S202, (g), a standard layer-number determination section).

Specifically, in the case of the optical measurement, the number of layers is determined based on the reflected-light intensities of the substrate and graphene.

For example, in the case where the substrate is made of $SiO_2$, when the reflected-light intensity of $SiO_2$ is regarded as 100%, the reflected-light intensity of graphene decreases by 6.45% as the number of layers increases by one. Therefore, based on the degree of decrease of the reflected-light intensity of graphene with respect to the reflected-light intensity of $SiO_2$, the number of layers of graphene is determined.

S202 corresponds to a preliminary process for simplifying the acquisition of the calibration-curve data 51, and therefore is not required to be performed.

Next, as illustrated in FIG. 11, the control section 43 directs the radiation of the electron beam to the substrate and graphene provided on the substrate under the same conditions as those in S103 based on the layer-number determination program 49 so that the radiation section 31 radiates the electron beam (primary electrons) (S203, (d), a standard electron-image acquiring section).

Next, the control section 43 controls the detection section 33 to acquire the reflected-electron image or the second-electron image (SEM image) of graphene (S204, (d), the standard electron-image acquiring section).

Next, as illustrated in FIG. 11, the relative intensity ratio of the substrate and the electron image of graphene is obtained (S205, (e), a standard intensity-ratio analysis section). A method of obtaining the relative intensity ratio is the same as that in S105.

Next, as illustrated in FIG. 11, the control section 43 determines whether or not the number of layers of graphene is known (specifically, whether or not S202 has been performed). When the number of layers is known, the processing proceeds to S207. When the number of layers is unknown, the processing proceeds to S208 (S206).

When the number of layers of graphene is known, the control section 43 plots the relationship between the number of layers of graphene and the relative intensity ratio and then performs fitting by using a method of least-squares or the like to create the calibration-curve data 51 and stores the calibration-curve data in the storage section 45 (S207, (f), a calibration-curve creating section).

When the number of layers of graphene is unknown, the control section 43 obtains an attenuation amount $\Delta$ of the relative intensity ratio (S208, (f), the calibration-curve creating section).

Specifically, for each graphene, its own secondary-electron relative intensity is sequentially divided by natural numbers starting from 1 to extract a common value which is obtained as the attenuation amount $\Delta$.

For example, a value of the attenuation amount $\Delta$ is about $5.8 \times 1.0^{-2}$ in the case where the substrate is the Si substrate with the SiO$_2$ film, about $1.8 \times 1.0^{-2}$ in the case where the substrate is the sapphire substrate, and about $3.3 \times 1.0^{-2}$ in the case where the substrate is the mica substrate. When the value of $\Delta$ is to be obtained, the effects of the instrumental function such as the absolute intensity of the primary electrons obtained by the SEM, a capture efficiency of the secondary electrodes, and the sensitivity characteristic of the secondary-electron detector can be eliminated by using the relative value of the secondary-electron intensity of graphene with respect to the secondary-electron intensity at the substrate surface. Therefore, even when using another SEM, the same result can be obtained. This point corresponds to important proof to prove generality and versatility of this invention.

Next, as illustrated in FIG. 11, the control section 43 determines the number of layers of graphene from the attenuation amount $\Delta$ (S209, (f), the calibration-curve creating section).

Specifically, the number of layers of graphene is determined in the following manner.

First, let a ratio of secondary-electron generating ability of the graphene 2 and that of the substrate 1 be $\alpha$. Then, as described above, the attenuation amount $\Delta$ generated with the passage through graphene is proportional to the number of layers of graphene, and therefore the intensities of the secondary electrons when graphene has one layer, two layers, three layers, four layers, . . . , and n layers are respectively $\alpha-1\Delta$, $\alpha-2\Delta$, $\alpha-3\Delta$, $\alpha-4\Delta$, . . . , and $\alpha-n\Delta$.

The value of $\alpha$ is determined when the kind of substrate is determined. Therefore, the number of layers of graphene is determined from $\alpha-n\Delta$.

When the number of layers of graphene is determined, the control section 43 plots the relationship between the number of layers of graphene and the relative intensity ratio and then performs fitting by using the method of least-squares or the like to create the calibration-curve data 51 and stores the calibration-curve data in the storage section 45 (S207, (f), the calibration-curve creating section).

The method of creating the calibration curve is described above.

As described above, according to this embodiment, the layer-number determining device 21 includes the measurement unit 23 for radiating the electron beam to graphene to measure the intensity of the reflected electrons or the secondary electrons generated thereby, and the layer-number determining unit 25 for determining the number of layers of the two-dimensional atomic layer thin film based on the intensity of the secondary electrons, measured by the measurement unit 23, and therefore determines the number of layers of graphene from the intensity of the reflected electrons or the secondary electrons generated by radiating the electron beam to graphene.

Thus, the layer-number determining device 21 can determine the number of layers of graphene in a more versatile manner as compared with the conventional cases.

EXAMPLES

In the following, this invention is more specifically described based on examples.

Example 1

The determination of the number of layers of graphene having an unknown number of layers was attempted by the method of determining the number of layers of graphene using the SEM (this invention) and the method of determining the number of layers of graphene using the optical technique (conventional example).

First, the determination of the number of layers of graphene using the SEM was performed in the following procedure.

First, graphene was stripped away from graphite with an adhesive tape and was applied onto an Si substrate with an SiO$_2$ film having a film thickness of 300 nm.

Next, an SEM image of graphene was acquired to determine the number of layers.

Figure 12:
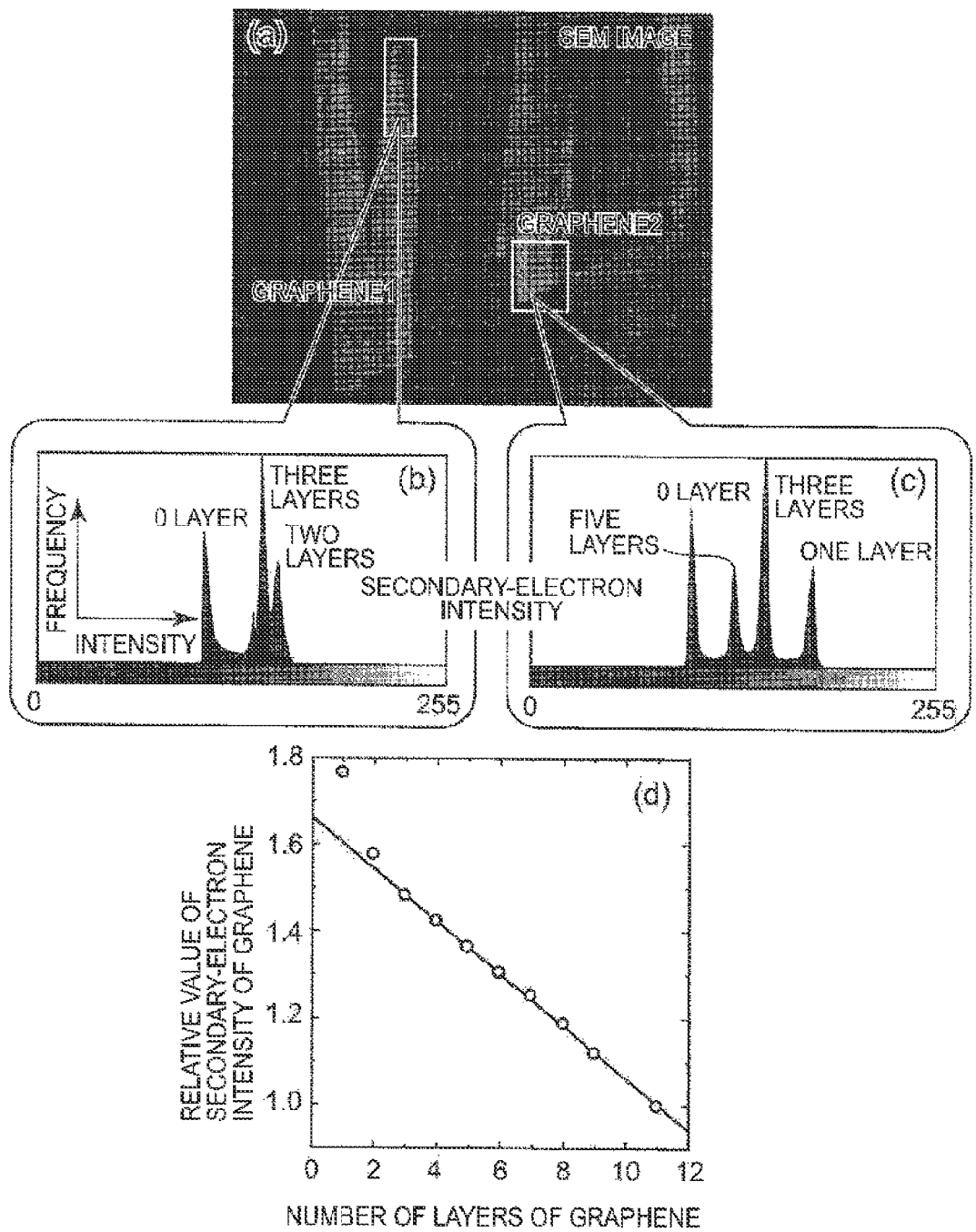
FIG. 12 are views illustrating a specific example of a method of determining the number of layers of graphene using an SEM.

For the image analysis, the SEM image was acquired as digital data so that a brightness in 256 gradations for each image pixel corresponded to the secondary-electron intensity. The results are shown in FIG. 12.

FIG. 12(a) is a view representing the SEM image, FIGS. 12(b) and 12(c) are histograms for portions surrounded by rectangles in FIG. 12(a), each having the horizontal axis representing the secondary-electron intensity and the vertical axis representing the frequency. FIG. 12(d) shows the relationship between the relative value of the secondary-electron intensity of graphene with respect to the secondary-electron intensity at the surface of underlying SiO$_2$ and the number of layers of graphene. A straight line in FIG. 12(d) is a calibration curve. The calibration curve was obtained by estimating the attenuation amount $\Delta$ by the analysis of the SEM images of graphene having various numbers of layers.

As is apparent from FIG. 12(a), qualitatively, graphene was observed as a distinct SEM image. From FIGS. 12(b) and 12(c), it has been found that the intensity of graphene is discretely distributed for each number of layers, and therefore graphene having different numbers of layers can be quantitatively evaluated as histograms distinctively separated from each other. Specifically, by using the calibration curve of FIG. 12(d), it is understood that the portion of the graphene 1, surrounded by the rectangle in FIG. 12(a), includes graphene having two layers and three layers as the number of layers and the portion of the graphene 2, surrounded by the rectangle, includes graphene having one layer, three layers, and five layers.

Next, the optical-microscope image of the above-mentioned samples was acquired to determine the number of layers.

Figure 13:
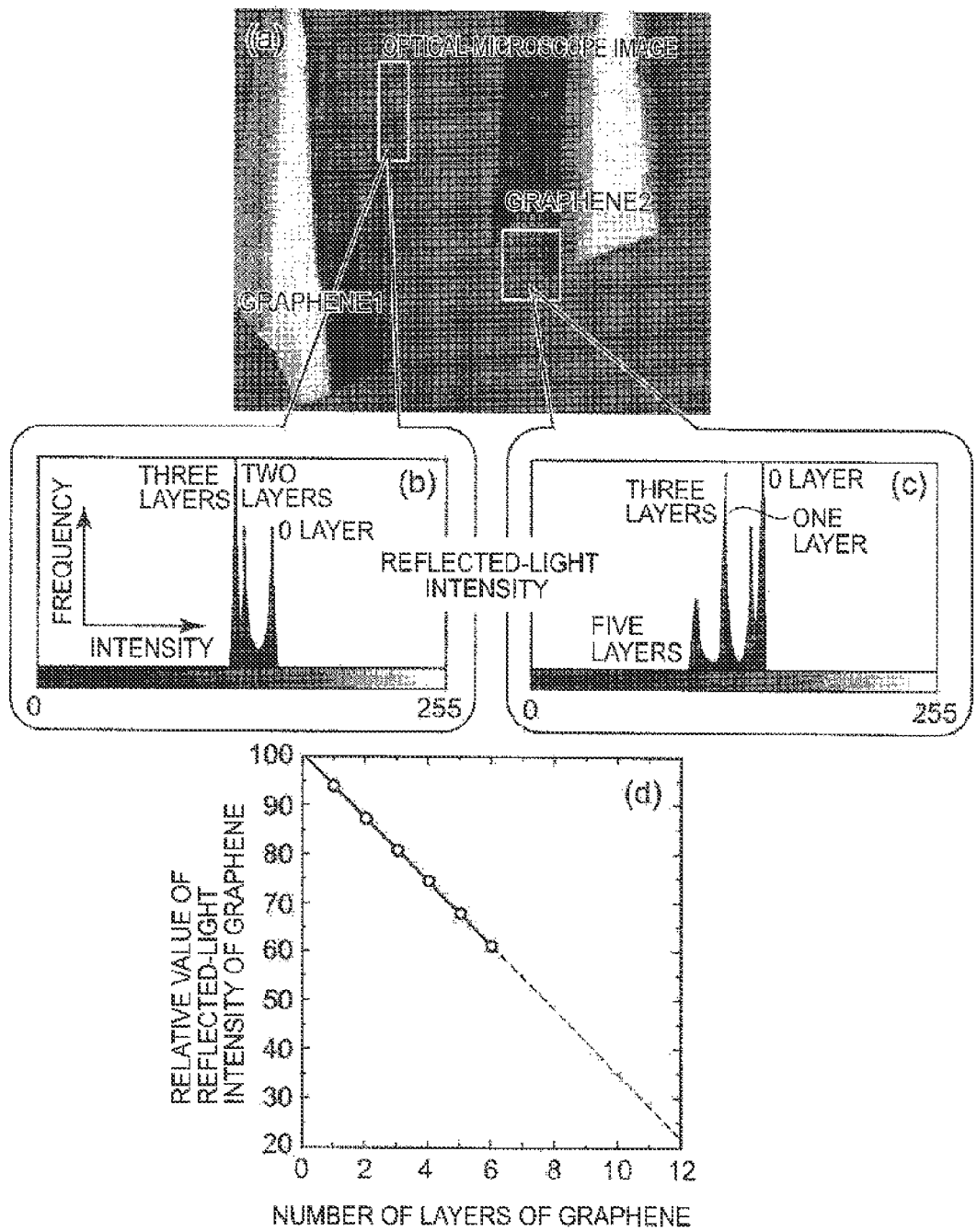
FIG. 13 are views illustrating a method of determining the number of layers of graphene with an optical technique.

The results are shown in FIG. 13.

FIG. 13(a) is a view representing the optical-microscope image, FIGS. 13(b) and 13(c) show the frequencies of the reflected-light intensities of portions surrounded by rectangles in FIG. 13(a), and FIG. 13(d) shows the relationship between the relative value of the reflected-light intensity of graphene with respect to the reflected-light intensity at the surface of underlying $SiO_2$ and the number of layers of graphene. As shown in FIG. 13(d), it is understood that graphene can be evaluated only up to about six layers by the optical means of the conventional technology.

From the above-mentioned results, with the method of determining the number of layers using the SEM image according to this invention, ten or larger number of layers of graphene can be evaluated. Therefore, the effectiveness and superiority of the method of determining the number of layers of graphene using the SEM image on the method of determining the number of layers of graphene using the optical means have been proved.

Example 2

In order to specify an effective range of the primary-electron accelerating voltage to be used to determine the number of layers of graphene using the SEM on the Si substrate with the $SiO_2$ film, the relationship between the relative value of the secondary-electron intensity with respect to that at the substrate surface of graphene and the number of layers of graphene was studied using various primary-electron accelerating voltages $V_{acc}$. The graphene samples were prepared in the same manner as in Example 1. The SEM measurement was carried out under the conditions where the $SiO_2$ film thickness was 300 nm, the number of layers of graphene was 1 to 11, and $V_{acc}$=0.5 to 20 kV. By the above-mentioned method, the graphene SEM images were analyzed to obtain the results shown in FIG. 14.

Figure 14:
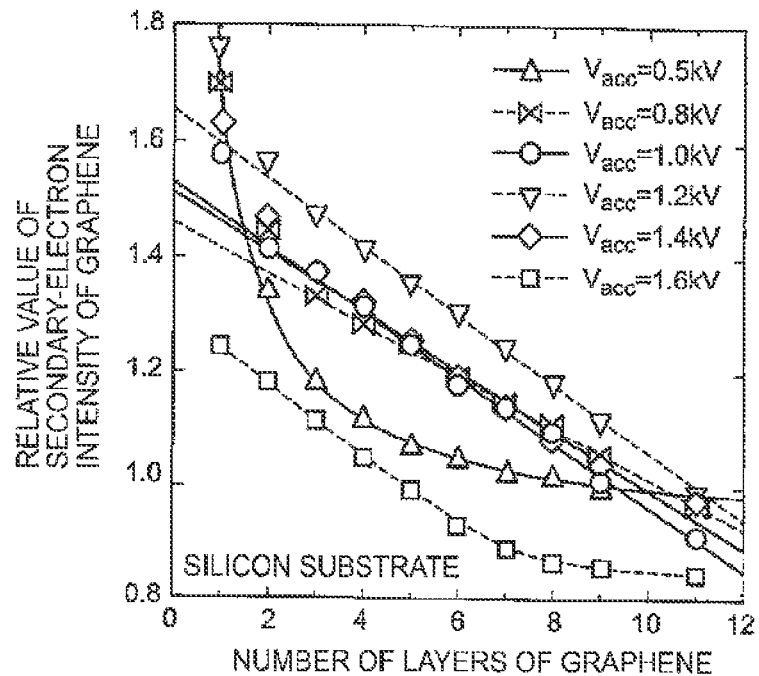
FIG. 14 is a graph showing the relationship between a relative value of a secondary-electron intensity to that at a substrate surface of graphene and the number of layers of graphene when an Si substrate with an $SiO_2$ film is used.

As shown in FIG. 14, it was in the cases where $V_{acc}$=0.8 kV, 1.0 kV, 1.2 kV, and 1.4 kV that the linearity was ensured between the relative value of the secondary-electron intensity of graphene and the number of layers of graphene over a wide range of the number of layers. On the other hand, with $V_{acc}$=0.5 kV, a non-linearity strongly appeared. With $V_{acc}$=1.6 kV, the linearity was obtained when the number of layers of graphene was up to about six. However, when the number of layers was seven or larger, the non-linearity appeared. Therefore, when the calibration-curve data 51 was to be obtained only by the SEM, it was assumed that the attenuation amount Δ did not depend on the number of layers, and therefore the effective range of $V_{acc}$ was 0.5 kV<$V_{acc}$<1.6 kV. However, when the calibration-curve data 51 was to be obtained by using the optical measurement, the Raman measurement, and the AFM measurement at the same time with the known number of layers, it was not necessary to directly obtain Δ. Therefore, $V_{acc}$<2.0 kV corresponding to a low accelerating-voltage range was the effective range of $V_{acc}$.

Example 3

In order to specify an effective range of the primary-electron accelerating voltage to be used to determine the number of layers of graphene using the SEM on the sapphire substrate, the relationship between the relative value of the secondary-electron intensity with respect to that at the substrate surface of graphene and the number of layers of graphene was studied using various $V_{acc}$. The graphene samples were prepared in the same manner as in Example 1. The SEM measurement was carried out under the conditions where the number of layers of graphene was 1 to 12 and $V_{acc}$=0.5 to 20 kV. By the above-mentioned method, the graphene SEM images were analyzed to obtain the results shown in FIG. 15.

Figure 15:
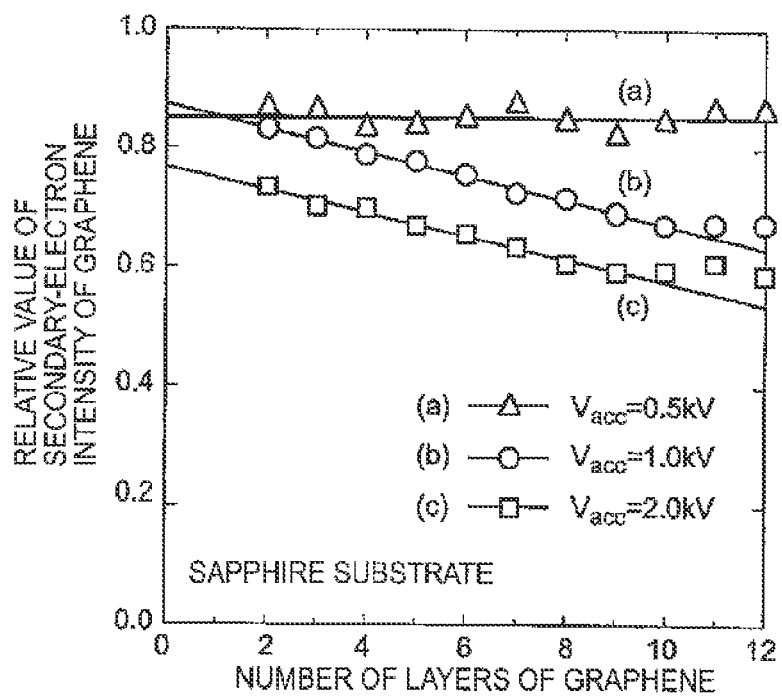
FIG. 15 is a graph showing the relationship between the relative value of the secondary-electron intensity to that at the substrate surface of graphene and the number of layers of graphene when a sapphire substrate is used.

As shown in FIG. 15, it was in the cases where $V_{acc}$=1.0 kV and 2.0 kV that the linearity was ensured between the relative value of the secondary-electron intensity of graphene and the number of layers of graphene. With $V_{acc}$=0.5 kV, the relative value of the secondary-electron intensity hardly depended on the number of layers. Therefore, it was found that the effective range of $V_{acc}$ was 0.5 kV<$V_{acc}$<2.0 kV when the sapphire substrate was used.

Example 4

In order to specify an effective range of the primary-electron accelerating voltage to be used to determine the number of layers of graphene using the SEM on the mica substrate, the relationship between the relative value of the secondary-electron intensity with respect to that at the substrate surface of graphene and the number of layers of graphene was studied using various $V_{acc}$. The graphene samples were prepared in the same manner as in Example 1. The SEM measurement was carried out under the conditions where the number of layers of graphene was 1 to 20 and $V_{acc}$=0.5 to 20 kV. By the above-mentioned method, the graphene SEM images were analyzed to obtain the results shown in FIG. 16.

Figure 16:
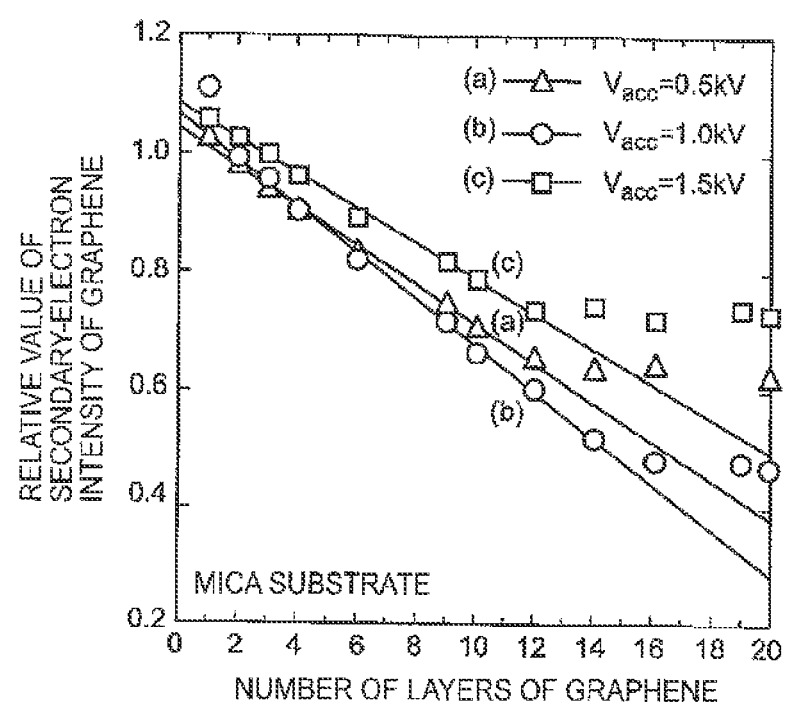
FIG. 16 is a graph showing the relationship between the relative value of the secondary-electron intensity to that at the substrate surface of graphene and the number of layers of graphene when a mica substrate is used.

As shown in FIG. 16, the linearity appeared between the relative value of the secondary-electron intensity of graphene and the number of layers of graphene in the range where graphene had up to twelve layers. However, when the number of layers exceeded twelve, the layer-number dependence was not observed. Therefore, it was found that the effective range of Vacc was 0.5 kV≤$V_{acc}$≤2.0 kV when the mica substrate was used.

Although the embodiment and examples of this invention have been specifically described above, this invention is not limited to the embodiment and examples described above. Various variations are possible based on the technical thought of this invention.

For example, although the description has been given and the experiments have been conducted taking graphene as an example of the two-dimensional atomic layer thin film in this embodiment and the examples, this invention is also applicable to materials other than graphene as long as the two-dimensional atomic layer thin film is used.

Moreover, although the device including the SEM and the computer has been exemplified as the layer-number determining device 21 in this embodiment, the configuration of the layer-number determining device is not limited to the above-mentioned configuration as long as the device can radiate the electron beam and is capable of analyzing the intensity of the secondary electrons or the reflected electrons.

Further, this application claims the benefit of priority from Japanese Patent Application No. 2010-145314, filed on Jun. 25, 2010, the disclosure of which is incorporated herein by reference in its entirety.

The invention claimed is:

1. A method of determining a number of layers of a two-dimensional thin film atomic structure, the method comprising:

(a) acquiring an electron image of reflected electrons or secondary electrons generated by irradiating an electron beam to a two-dimensional atomic layer thin film having an unknown number of layers and a substrate supporting the two-dimensional atomic layer thin film;

(b) obtaining a relative intensity ratio of the electron image of the two-dimensional atomic layer thin film to an electron image of the substrate; and (c) determining the number of layers of the two-dimensional atomic layer thin film based on the relative intensity ratio.

2. A method of determining a number of layers of a two-dimensional thin film atomic structure according to claim 1, wherein the (c) comprises using a calibration curve indicating a relationship between the relative intensity ratio and the number of layers to determine the number of layers corresponding to the relative intensity ratio obtained in the (b) on the calibration curve as the number of layers of the two-dimensional atomic layer thin film having the unknown number of layers.

3. A method of determining a number of layers of a two-dimensional thin film atomic structure according to claim 1, further comprising:

(d) acquiring electron images of the reflected electrons or the secondary electrons generated by irradiating the electron beam to a plurality of two-dimensional atomic layer thin films having different numbers of layers and a substrate supporting the two-dimensional atomic layer thin films;

(e) obtaining relative intensity ratios of the electron images of the plurality of two-dimensional atomic layer thin films to the electron image of the substrate; and (f) creating a calibration curve by plotting a relationship between the relative intensity ratios of the electron images of the plurality of two-dimensional atomic layer thin films and the number of layers, wherein the (c) comprises using the calibration curve created in the (f) to determine the number of layers of the two-dimensional atomic layer thin film having the unknown number of layers.

4. A method of determining a number of layers of a two-dimensional thin film atomic structure according to claim 3, wherein the (f) comprises sequentially dividing, by natural numbers starting from 1, each of the relative intensity ratios of the electron images of the plurality of two-dimensional atomic layer thin films is to extract a common value so as to obtain a change amount $\Delta$ of the relative intensity ratio for one layer to create the calibration curve by using a relative intensity ratio corresponding to an integral multiple of the change amount $\Delta$ as a relative intensity ratio for each layer.

5. A method of determining a number of layers of a two-dimensional thin film atomic structure according to claim 3, further comprising (g) pre-determining the numbers of layers of the plurality of two-dimensional atomic layer thin films having different numbers of layers by an optical method of measuring a reflectance or of measuring a transmissivity, wherein the (f) comprises creating the calibration curve from the numbers of layers determined in the (g) and the relative intensity ratios measured in the (e).

6. A method of determining a number of layers of a two-dimensional thin film atomic structure according to claim 1, wherein the substrate comprises any one of a silicon substrate, a sapphire substrate, and a mica substrate.

7. A method of determining a number of layers of a two-dimensional thin film atomic structure according to claim 1, wherein the two-dimensional thin film atomic structure comprises graphene.

8. A layer-number determining device for a two-dimensional thin film atomic structure, the layer-number determining device comprising:

an electron-image acquiring section for acquiring an electron image of reflected electrons or secondary electrons generated by irradiating an electron beam to a two-dimensional atomic layer thin film having an unknown number of layers and a substrate supporting the two-dimensional atomic layer thin film;

an intensity-ratio analysis section for obtaining a relative intensity ratio of the electron image of the two-dimensional atomic layer thin film to an electron image of the substrate; and a layer-number determining section for determining the number of layers of the two-dimensional atomic layer thin film based on the relative intensity ratio.

9. A layer-number determining device for a two-dimensional thin film atomic structure according to claim 8, wherein the layer-number determining section uses a calibration curve indicating a relationship between the relative intensity ratio and the number of layers to determine the number of layers corresponding to the relative intensity ratio obtained by the intensity-ratio analysis section on the calibration curve as the number of layers of the two-dimensional atomic layer thin film having the unknown number of layers.

10. A layer-number determining device for a two-dimensional thin film atomic structure according to claim 8, further comprising:

a standard electron-image acquiring section for acquiring electron images of the reflected electrons or the secondary electrons generated by irradiating the electron beam to a plurality of two-dimensional atomic layer thin films having different numbers of layers and a substrate supporting the two-dimensional atomic layer thin films;

a standard intensity-ratio analysis section for obtaining relative intensity ratios of the electron images of the plurality of two-dimensional atomic layer thin films to the electron image of the substrate; and a calibration-curve creating section for creating a calibration curve by plotting a relationship between the relative intensity ratios of the electron images of the plurality of two-dimensional atomic layer thin films and the number of layers, wherein the layer-number determining section uses the calibration curve created by the calibration-curve creating section to determine the number of layers of the two-dimensional atomic layer thin film having the unknown number of layers.

11. A layer-number determining device for a two-dimensional thin film atomic structure according to claim 10, wherein the calibration-curve creating section sequentially divides, by natural numbers starting from 1, each of the relative intensity ratios of the electron images of the plurality of two-dimensional atomic layer thin films to extract a common value so as to obtain a change amount $\Delta$ of the relative intensity ratio for one layer to create the calibration curve by using a relative intensity ratio corresponding to an integral multiple of the change amount $\Delta$ as a relative intensity ratio for each layer.

12. A layer-number determining device for a two-dimensional thin film atomic structure according to claim 10, further comprising a standard layer-number determination section for pre-determining the numbers of layers of the plurality of two-dimensional atomic layer thin films having different numbers of layers by an optical method of measuring a reflectance or of measuring a transmissivity, wherein the calibration-curve creating section creates the calibration curve from the numbers of layers determined by the standard layer-number determination section and the relative intensity ratios measured by the standard intensity-ratio analysis section.

13. A layer-number determining device for a two-dimensional thin film atomic structure according to claim 8, wherein the substrate comprises any one of a silicon substrate, a sapphire substrate, and a mica substrate.

14. A layer-number determining device for a two-dimensional thin film atomic structure according to claim 8, wherein the two-dimensional thin film atomic structure comprises graphene.

* * * * *

UNITED STATES PATENT AND TRADEMARK OFFICE
CERTIFICATE OF CORRECTION

PATENT NO.         : 8,698,077 B2
APPLICATION NO.    : 13/704670
DATED              : April 15, 2014
INVENTOR(S)        : Hidefumi Hiura, Kazuhito Tsukagoshi and Hisao Miyazaki It is certified that error appears in the above-identified patent and that said Letters Patent is hereby corrected as shown below:

On the Title Page

Page 2, Column 1 Item (56) (Other Publications), Line 9: Delete "Numbre" and insert -- Number --

In the Specification

Column 2, Line 31: Delete "minor" and insert -- mirror --

Column 9, Line 53: Delete "α-4Δ4." and insert -- α-4Δ. --

Signed and Sealed this
Twenty-first Day of October, 2014

Michelle K. Lee
*Deputy Director of the United States Patent and Trademark Office*